(12) United States Patent
Dean et al.

(10) Patent No.: US 7,282,500 B2
(45) Date of Patent: Oct. 16, 2007

(54) IMIDAZOLE-2-CARBOXAMIDE DERIVATIVES AS RAF KINASE INHIBITORS

(75) Inventors: David Kenneth Dean, Harlow (GB); Andrew Kenneth Takle, Harlow (GB); David Matthew Wilson, Harlow (GB)

(73) Assignee: SmithKline Beecham P.L.C., Middlesex (GB)

( * ) Notice: Subject to any disclaimer, the term of this patent is extended or adjusted under 35 U.S.C. 154(b) by 283 days.

(21) Appl. No.: 10/478,153

(22) PCT Filed: May 20, 2002

(86) PCT No.: PCT/GB02/02353

§ 371 (c)(1),
(2), (4) Date: Nov. 19, 2003

(87) PCT Pub. No.: WO02/094808

PCT Pub. Date: Nov. 28, 2002

(65) Prior Publication Data

US 2004/0127496 A1    Jul. 1, 2004

(30) Foreign Application Priority Data

May 19, 2001    (GB) .................. 0112348.8

(51) Int. Cl.
*A61K 31/5377* (2006.01)
*C07D 401/14* (2006.01)
*C07D 413/14* (2006.01)

(52) U.S. Cl. ............. 514/235.8; 544/124; 544/131

(58) Field of Classification Search ............... 544/124; 514/235.8; 546/131
See application file for complete search history.

(56) References Cited

U.S. PATENT DOCUMENTS

| | | |
|---|---|---|
| 3,707,475 A | 12/1972 | Lombardino |
| 3,940,486 A | 2/1976 | Fitzi |
| 4,348,404 A | 9/1982 | Whitney |
| 4,447,431 A | 5/1984 | Sallmann |
| 4,735,958 A | 4/1988 | Roth et al. |
| 5,166,214 A | 11/1992 | Billheimer et al. |
| 5,179,117 A | 1/1993 | Maduckuie, Jr. |
| 5,227,486 A | 7/1993 | Merce-Vidal et al. |
| 5,236,917 A | 8/1993 | Dunlap et al. |
| 5,302,610 A | 4/1994 | Manning et al. |
| 5,310,748 A | 5/1994 | Wilde et al. |
| 5,514,505 A | 5/1996 | Limburg et al. |
| 5,552,557 A | 9/1996 | Fujii et al. |
| 5,593,991 A | 1/1997 | Adams et al. |
| 5,620,999 A | 4/1997 | Weier et al. |
| 5,656,644 A | 8/1997 | Adams et al. |
| 5,665,753 A | 9/1997 | Frazee et al. |
| 5,717,100 A | 2/1998 | Selnick et al. |
| 5,733,882 A | 3/1998 | Carr et al. |
| 5,776,954 A | 7/1998 | deLaszlo et al. |
| 5,792,778 A | 8/1998 | deLaszlo et al. |
| 5,837,719 A | 11/1998 | deLaszlo et al. |
| 5,859,041 A | 1/1999 | Liverton et al. |
| 5,861,420 A | 1/1999 | Reitz et al. |
| 5,880,139 A | 3/1999 | Chang |
| 5,932,576 A | 8/1999 | Anantanarayan et al. |
| 5,939,421 A | 8/1999 | Palanki et al. |
| 5,945,418 A | 8/1999 | Bemis et al. |
| 5,965,583 A | 10/1999 | Beers et al. |
| 6,008,235 A | 12/1999 | Adams et al. |
| 6,040,320 A | 3/2000 | Beers et al. |
| 6,087,381 A | 7/2000 | Hanson et al. |
| 6,096,753 A | 8/2000 | Spohr et al. |
| 6,136,828 A | 10/2000 | Elliott |
| 6,147,080 A | 11/2000 | Bemis et al. |
| 6,150,372 A | 11/2000 | Palanki et al. |
| 6,180,643 B1 | 1/2001 | Zablocki et al. |
| 6,207,687 B1 | 3/2001 | Claiborne et al. |
| 6,214,830 B1 | 4/2001 | Beers et al. |
| 6,235,760 B1 | 5/2001 | Feuerstein |
| 6,316,464 B1 | 11/2001 | Cheng et al. |

(Continued)

FOREIGN PATENT DOCUMENTS

DE    3935514    5/1991

(Continued)

OTHER PUBLICATIONS

U.S. Appl. No. 11/388,058, Adams et al. U.S. Appl. No. 11/388,058 is con. Of U.S. Appl. No. 10/432,092, filed Mar. 23, 2006.

(Continued)

*Primary Examiner*—Patricia L. Morris
(74) *Attorney, Agent, or Firm*—Grace C. Hsu; Mary E. McCarthy; Charles M. Kinzig

(57) ABSTRACT

The present invention relates to compounds of formula (I):

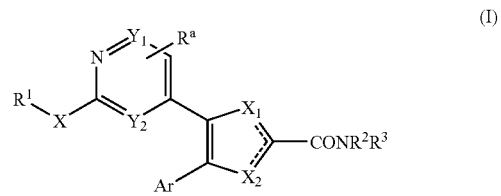

or pharmaceutically acceptable salts thereof, corresponding pharmaceutical compositions, use as Raf Kinase Inhibitors and treatment methods for neurotraumatic diseases and cancer.

5 Claims, No Drawings

U.S. PATENT DOCUMENTS

| | | | |
|---|---|---|---|
| 6,335,336 B1 | 1/2002 | Anantanarayan et al. | |
| 6,342,510 B1 | 1/2002 | Isakson et al. | |
| 6,423,713 B1 | 7/2002 | Anantanarayan et al. | |
| 6,436,966 B1 | 8/2002 | Ohkawa et al. | |
| 6,440,973 B1 | 8/2002 | Zablocki et al. | |
| 6,479,507 B2 | 11/2002 | Cheng et al. | |
| 6,503,930 B1 | 1/2003 | Hanson et al. | |
| 6,514,977 B1 | 2/2003 | Anantanarayan et al. | |
| 6,521,655 B1 | 2/2003 | Beers et al. | |
| 6,525,059 B1 | 2/2003 | Anantanarayan et al. | |
| 6,545,009 B1 | 4/2003 | Sugiyama et al. | |
| 6,548,520 B1 | 4/2003 | Adams et al. | |
| 6,579,873 B2 | 6/2003 | Anantanarayan et al. | |
| 6,602,877 B1 | 8/2003 | Banborough et al. | |
| 6,605,634 B2 | 8/2003 | Zablocki et al. | |
| 6,608,060 B1 | 8/2003 | Bemis et al. | |
| 6,617,324 B1 | 9/2003 | Naraian et al. | |
| 6,649,604 B2 | 11/2003 | Spohr et al. | |
| 6,852,740 B2 | 2/2005 | Hanson et al. | |
| 6,979,686 B1 | 12/2005 | Naraian et al. | |
| 6,987,119 B2 * | 1/2006 | Gaiba et al. | 514/341 |
| 7,019,005 B2 | 3/2006 | Naraian et al. | |
| 7,071,198 B1 | 7/2006 | Naraian et al. | |
| 7,153,959 B2 | 12/2006 | Naraian et al. | |
| 2001/0044538 A1 | 11/2001 | Cheng et al. | |
| 2002/0013354 A1 | 1/2002 | Cheng et al. | |
| 2002/0086869 A1 | 7/2002 | Anantanarayan et al. | |
| 2003/0096819 A1 | 5/2003 | Zablocki et al. | |
| 2003/0134837 A1 | 7/2003 | Gaiba et al. | |
| 2003/0139462 A1 | 7/2003 | Cheng et al. | |
| 2003/0144529 A1 | 7/2003 | Hanson et al. | |
| 2003/0153588 A1 | 8/2003 | Steadman et al. | |
| 2004/0038964 A1 | 2/2004 | Dean et al. | |
| 2004/0053943 A1 | 3/2004 | Adams et al. | |
| 2004/0106668 A1 | 6/2004 | Gregory et al. | |
| 2004/0127496 A1 | 7/2004 | Dean et al. | |
| 2004/0147579 A1 | 7/2004 | Naraian et al. | |
| 2004/0176433 A1 | 9/2004 | Naraian et al. | |
| 2004/0192689 A1 | 9/2004 | Dean et al. | |
| 2004/0198730 A1 | 10/2004 | Dean et al. | |
| 2004/0209883 A1 | 10/2004 | Bamford et al. | |
| 2004/0235843 A1 | 11/2004 | Bamford et al. | |
| 2004/0248896 A1 | 12/2004 | Dean et al. | |
| 2004/0254186 A1 | 12/2004 | Dean et al. | |
| 2005/0009844 A1 | 1/2005 | Bemis et al. | |
| 2005/0043355 A1 | 2/2005 | Gregory et al. | |
| 2006/0235014 A1 | 10/2006 | Bemis et al. | |

FOREIGN PATENT DOCUMENTS

| | | |
|---|---|---|
| EP | 0044486 | 1/1982 |
| EP | 0653421 | 5/1995 |
| GB | 2 306 108 | 4/1997 |
| GB | 2 306 108 A | 4/1997 |
| JP | 112 46 437 | 9/1999 |
| WO | WO91/18885 | 12/1991 |
| WO | WO93/23381 | 11/1993 |
| WO | WO95/03297 | 2/1995 |
| WO | WO96/03387 | 2/1996 |
| WO | WO96/41645 | 12/1996 |
| WO | WO97/05878 | 2/1997 |
| WO | WO97/12876 | 4/1997 |
| WO | WO 97/12876 | 4/1997 |
| WO | WO97/16441 | 5/1997 |
| WO | WO97/16442 | 5/1997 |
| WO | WO97/24119 | 7/1997 |
| WO | WO97/35855 | 10/1997 |
| WO | WO97/36587 | 10/1997 |
| WO | WO97/47618 | 12/1997 |
| WO | WO97/48672 | 12/1997 |
| WO | WO98/13278 | 4/1998 |
| WO | WO98/16227 | 4/1998 |
| WO | WO98/18788 | 5/1998 |
| WO | WO98/47899 | 10/1998 |
| WO | WO98/52558 | 11/1998 |
| WO | WO98/56788 | 12/1998 |
| WO | WO99/01449 | 1/1999 |
| WO | WO99/03837 | 1/1999 |
| WO | WO99/25717 | 5/1999 |
| WO | WO99/32436 | 7/1999 |
| WO | WO99/32455 | 7/1999 |
| WO | WO99/61437 | 12/1999 |
| WO | WO 00/01688 | 1/2000 |
| WO | WO 00/06563 | 2/2000 |
| WO | WO 00/25791 | 5/2000 |
| WO | WO 00/26209 | 5/2000 |
| WO | WO 00/33836 | 6/2000 |
| WO | WO 00/06124 | 11/2000 |
| WO | WO 00/64422 | 11/2000 |
| WO | JP 2001/181187 | 3/2001 |
| WO | WO 01/34149 | 5/2001 |
| WO | WO 01/34150 | 5/2001 |
| WO | WO 01/37835 | 5/2001 |
| WO | WO 01/38324 | 5/2001 |
| WO | WO 01/66539 | 9/2001 |
| WO | WO 01/66540 | 9/2001 |
| WO | WO 01/87877 | 11/2001 |
| WO | WO 02/024680 | 3/2002 |
| WO | WO 02/39954 | 5/2002 |
| WO | WO 02/057255 | 7/2002 |
| WO | WO 02/094808 | 11/2002 |
| WO | WO 03/022832 | 3/2003 |
| WO | WO 03/022836 | 3/2003 |
| WO | WO 03/022837 | 3/2003 |
| WO | WO 03/022838 | 3/2003 |
| WO | WO 03/022840 | 3/2003 |
| WO | WO 03/022883 | 3/2003 |

OTHER PUBLICATIONS

U.S. Appl. No. 11/333,033, Steadman et al. U.S. Appl. No. 11/333,033 is con. Of U.S. Appl. No. 10/220,674, filed Jan. 17, 2006.

Adams et al., *Bioorganic & Medical Chemistry Letters*, vol. 8, pp. 3111-3116, (1998).

Adams et al., *Current Opinion in Drug Discovery and Development*, vol. 2(2), pp. 96-109, (1999).

Alves, et al., *Tetrahedron Letters*, vol. 29, pp. 2135-2136, (1988).

Antolini et al., *Bioorganic & Medical Chemistry Letters*, vol. 9, pp. 1023-1028, (1999).

Ashley Publications, "Two Novel structural classes of p38 Kinase inhibitors," *Exp Opin. Ther. Patents* vol. 9(4) pp. 477-480, (1999).

Ashley Publications, "p38 Inhibitors based on the pyridylurea and pyridylacetoamide templates," *Exp Opin. Ther. Patents*, vol. 10(7), pp. 1151-1154, (2000).

Astles et al., *J. Med. Chem.*, vol. 39, pp. 1423-1432, (1996).

Bilodeau et al., *J. Org. Chem.*, vol. 63, pp. 2800-2801, (1998).

Boehm et al., *Exp Opinion Ther. Patents*, vol. 10(1) pp. 25-37, (2000).

Boehm et al., *J. Med Chem.*, vol. 39, pp. 3929-3937, (1996).

Cascieri et al., *The Journal of Biological Chemistry*, vol. 274, No. 13, pp. 8694-8697, Issue of (Mar. 26, 1999).

Claiborne et al., *Tetrahedron Letters*, vol. 39, pp. 8939-8942, (1998).

Cohen et al., *Journal of the National Cancer Inst.*, vol. 95, No. 8, (Apr. 16, 2003).

Cuenda et al., *FEBS Letters*, vol. 364, pp. 229-233, (1995).

Davies et al., *Nature*, vol. 417, pp. 949-954, (Jun. 27, 2002).

de Laszlo et al., *Bioorganic & Medical Chemistry Letters*, vol. 8, pp. 2689-2694, (1998).

de Laszlo et al., *Bioorganic & Medical Chemistry Letters*, vol. 9, pp. 641-646, (1999).

Dumas et al., *Bioorganic & Medical Chemistry Letters*, vol. 10, pp. 2047-2050, (2000).

Dumas et al., *Bioorganic & Medical Chemistry Letters*, vol. 10, pp. 2051-2054 (2000).
Eberwein et al., *Clinical Cancer Research*, vol. 6 (Supple.) Poster session 17, p. 4547,(406), (Nov. 2000).
Echavarres et al., *J. Amer. Chem. Soc.*, vol. 109, pp. 5478-5486, (1978).
Engel et al., *Liebigs Ann. Chem.*, pp. 1916-1927, (1978).
Fischer et al., *Rec.Trav.Chim.Pays.Bas.*, vol. 84, pp. 439-440, (1965).
Gallagher et al., *Bioorganic & Medical Chemistry*, vol. 5(1), pp. 49-64, (1997).
Garcia-Echeverria et al., *Med. Res. Reviews*, vol. 20(1) pp. 28-57, (2000).
Garigipati, R., *Tetrahedron Letters*, vol. 31(14) pp. 1969-1972, (1990).
Hall-Jackson et al., *Oncogene*, vol. 18, pp. 2047-2054, (1999).
Heimbrook et al., "Identification of Potent, Selective Inhibitors of Raf Protein Kinase," *Amer. Assoc. for Cancer Res. New Orleans*, Abstract 3793, (Apr. 1998).
Henry et al., *Bioorganic & Medical Chemistry Letters*, vol. 8, pp. 3335-3340, (1998).
Henry et al., *Drugs of the Future*, vol. 24(12), pp. 1345-1354, (1999).
Ishibashi, *Chem. Pharm. Bull.*, vol. 37(8), pp. 2214-2216, (1989).
Ishikura et al., M., *Chem.Pharm. Bull.*, vol. 11, pp. 4755-4763, (1985).
Johnson, *J. Chem Soc.*, Perkin Trans., vol. 1, pp. 895-905, (1996).
Kalmes et al., *Febs Letters*, vol. 444, No. 1, pp. 71-74, (1999).
Katritzky, *Synthesis*, pp. 45-47, (1993).
Lackey et al., *Bioorganic & Medical Chemistry Letters*, vol. 10, pp. 223-226, (2000).
Lee et al., *Pharmacol Ther.*, vol. 82(2-3), pp. 389-397, (1999).
Lisnock et al., *BioChemistry*, vol. 37, pp. 16573-16581, (1998).
Liverton et al., J. Med. Chem., vol. 42, No. 12, pp. 2180-2190, (199).
Lowinger et al., Clinical Cancer Research, vol. 6(No. 335) (Suppl.) Poster session 13, p. 4533, (Nov. 2000).
Minato et al., *Tetrahedron Letters*, vol. 22, pp. 5319-5322, (1981).
Morton et al., *Tetrahedron Letters*, pp. 4123-4124, (1982).
Pridgen, *J. Org. Chem.*, vol. 47, pp. 4319-4323, (1982).
Revesz et al., *Bioorganic & Medical Chemistry Letters*, vol. 10, pp. 1261-1264, (2000).
Salituro et al., *Current Medicinal Chemistry*, vol. 6, pp. 807-823, (1999).
Soni, *Aust. J. Chem.*, vol. 35, pp. 1493-1496, (1982).
Stover et al., *Current Opinion in Drug Discovery and Development*, vol. 2(4), pp. 274-285, (1999).
Strzybny et al., *J. Org. Chem.*, vol. 28, pp. 3381-3383, (1963).
Tannapfel et al., *GUT BMJ Journals*, vol. 52, pp. 706-712, (2003).
Thompson, et al., *J. Org. Chem.*, vol. 49, pp. 5237-5243, (1984).
Toledo et al., *Current Medicinal Chemistry*, vol. 6 pp. 775-805, (1999).
Tong et al., *Nature Structural Biology*, vol. 4(4) pp. 311-316, (1997).
Uno, *Bull. Chem. Soc. Japan.*, vol. 69, pp. 1763-1767, (1996).
VanLeusen et al., *J.O.C.*, vol. 42, (7) pp. 1153-1159, (1977).
Wang et al., *Structure*, vol. 6(9), pp. 1117-1128, (Sep. 15, 1998).
Young et al., *The Journal of Biological Chemistry*, vol. 272(18), pp. 12116-12121, (1997).
Zavyalov, et al., *Khim Farm Zh*, vol. 26(3), p. 88, (1992) (With Translation).
Wermuth, C.G. (ed.), "Chapter 13: Molecular Variations Based on Isosteric Replacements", *The Practice of Medicinal Chemistry*, pp. 204-237, Academic Press Ltd., Copyright (1996), XP-002190259.
DE 3935514—Derwent Abstract No. 1991-133717/19.
JP 112 46 437—Derwent Abstract No. 1999-566491/48.

* cited by examiner

IMIDAZOLE-2-CARBOXAMIDE DERIVATIVES AS RAF KINASE INHIBITORS

This invention relates to novel compounds and their use as pharmaceuticals particularly as Raf kinase inhibitors for the treatment of neurotraumatic diseases.

Raf protein kinases are key components of signal transduction pathways by which specific extracellular stimuli elicit precise cellular responses in mammalian cells. Activated cell surface receptors activate ras/rap proteins at the inner aspect of the plasmamembrane which in turn recruit and activate Raf proteins. Activated Raf proteins phosphorylate and activate the intracellular protein kinases MEK1 and MEK2. In turn, activated MEKs catalyse phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g. histiocytic lymphoma, lung adenocarcinoma, small cell lung cancer and pancreatic and breast carcinoma; and also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth.

We have now found a group of novel compounds that are inhibitors of Raf kinases, in particular inhibitors of B-Raf kinase.

According to the invention there is provided a compound of formula (I):

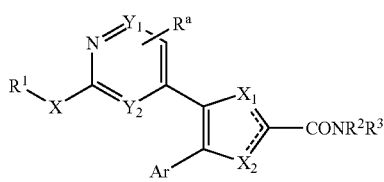

wherein
X is O, $CH_2$, S or NH, or the moiety X—$R^1$ is hydrogen;
$Y_1$ and $Y_2$ independently represent CH or N;
$R^1$ is hydrogen, $C_{1-6}$alkyl, $C_{3-7}$cycloalkyl, aryl, aryl$C_{1-6}$alkyl, heterocyclyl, heterocyclyl$C_{1-6}$alkyl, heteroaryl, or heteroaryl$C_{1-6}$alkyl any of which except hydrogen, may be optionally substituted;
$R^2$ and $R^3$ independently represent hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl, or $R^2$ and $R^3$ together with the nitrogen atom to which they are attached form a 4- to 10-membered monocyclic or bicyclic ring;

Ar is a group of the formula a) or b):

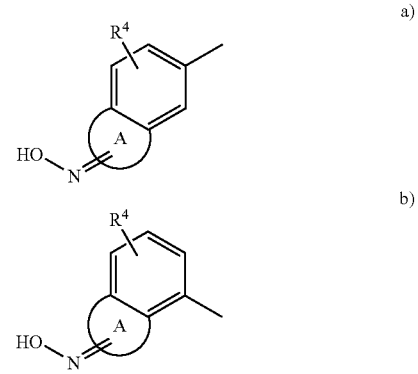

wherein A represents a fused 5- to 7-membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto;
$R^a$ and $R^4$ are independently selected from hydrogen, halogen, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N—$C_{1-6}$alkylamino, acylamino, arylcarbonylamino, acyloxy, carboxy, carboxy salts, carboxy esters, carbamoyl, mono- and di-N—$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkyl sulphinyl or $C_{1-6}$alkylsulphonyl; and
one of $X_1$ and $X_2$ is N and the other is $NR^6$, wherein $R^6$ is hydrogen, $C_{1-6}$alkyl, or aryl$C_{1-6}$alkyl;
or a pharmaceutically acceptable salt thereof.

As used herein, the double bond indicated by the dotted lines of formula (I), represent the possible tautomeric ring forms of the compounds falling within the scope of this invention, the double bond being to the unsubstituted nitrogen atom.

The hydroxyimino moiety can be positioned on any of carbon atoms of the non-aromatic ring in groups a) and b).

The hydroxyimino moiety can exist as either the E or Z isomer or as a mixture of both.

Alkyl and alkenyl groups referred to herein, individually or as part of larger groups e.g. alkoxy, may be straight or branched groups containing up to six carbon atoms and are optionally substituted by one or more groups selected from the group consisting of aryl, heteroaryl, heterocyclyl, $C_{1-6}$alkoxy, $C_{1-6}$alkylthio, aryl$C_{1-6}$alkoxy, aryl$C_{1-6}$alkylthio, amino, mono- or di-$C_{1-6}$alkylamino, cycloalkyl, cycloalkenyl, carboxy and esters thereof, amide, sulphonamido, ureido, guanidino, $C_{1-6}$alkylguanidino, amidino, $C_{1-6}$alkylamidino, $C_{1-6}$ acyloxy, azido, hydroxy, hydroxyimino and halogen.

Cycloalkyl and cycloalkenyl groups referred to herein include groups having from three to seven ring carbon atoms and are optionally substituted as described hereinabove for alkyl and alkenyl groups.

When used herein, the term "aryl" includes, unless otherwise defined, single and fused rings suitably containing from 4 to 7, preferably 5 or 6, ring atoms in each ring, which rings, may each be unsubstituted or substituted by, for example, up to three substituents.

Suitable aryl groups include phenyl and naphthyl such as 1-naphthyl or 2-naphthyl.

Optional substituents for alkyl, alkenyl, cycloalkyl and cycloalkenyl groups include aryl, heteroaryl, heterocyclyl, $C_{1-6}$alkoxy, $C_{1-6}$alkylthio, aryl$C_{1-6}$alkoxy, aryl$C_{1-6}$alkylthio, amino, mono-or di-$C_{1-6}$alkylamino, aminosulphonyl, cycloalkyl, cycloalkenyl, carboxy and esters thereof, amide, ureido, quanidino, $C_{1-6}$alkylquanidino, amidino, $C_{1-6}$alkylamidino, $C_{1-6}$acyloxy, hydroxy, and halogen or any combination thereof.

When used herein the term "heterocyclyl" includes, unless otherwise defined, non-aromatic, single and fused, rings suitably containing up to four heteroatoms in each ring, each of which is selected from O, N and S, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of heterocyclyl groups include pyrrolidine, piperidine, piperazine, morpholine, imidazolidine and pyrazolidine.

When used herein, the term "heteroaryl" includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms. A bicyclic heteroaromatic ring system may include a carbocyclic ring. Examples of heteroaryl groups include pyrrole, quinoline, isoquinoline, pyridine, pyrimidine, oxazole, thiazole, thiadiazole, triazole, imidazole and benzimidazole.

Aryl, heterocyclyl and heteroaryl groups may be optionally substituted by preferably up to three substituents. Suitable substituents include halogen, $C_{1-6}$alkyl, aryl, aryl $C_{1-6}$alkyl, $C_{1-6}$alkoxy, $C_{1-6}$alkoxy $C_{1-6}$alkyl, halo $C_{1-6}$alkyl, aryl$C_{1-6}$alkoxy, hydroxy, nitro, cyano, azido, amino, mono- and di-N—$C_{1-6}$alkylamino, acylamino, arylcarbonylamino, acyloxy, carboxy, carboxy salts, carboxy esters, carbamoyl, mono- and di-N—$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl, $C_{1-6}$alkylsulphonyl, heterocyclyl, heteroaryl, heterocyclyl $C_{1-6}$alkyl, hydroxyimino-$C_{1-6}$alkyl and heteroaryl $C_{1-6}$alkyl, and combinations thereof.

Preferably the optional substituent contains a solubilising group; suitable solubilising moieties will be apparent to those skilled in the art and include hydroxy and amine groups. Even more preferably the optional substituent includes amino, mono- or di-$C_{1-6}$alkylamino, amine containing heterocyclyl, and hydroxy or any combination thereof.

X is preferably NH or X—$R^1$ is preferably hydrogen and when X is NH, $R^1$ is preferably hydrogen or $C_{1-6}$alkyl.

When $Y_1$ and $Y_2$ are CH, X—$R^1$ is preferably hydrogen.
When $Y_2$ is N, X—$R^1$ is preferably $NH_2$.
Preferably $R^6$ is hydrogen.
Most preferably X—$R^1$ is hydrogen A is preferrably a fused 5 membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto.

Even more preferably A is a a fused 5 membered ring.
Preferably $R^2$ and $R^3$ independently represent hydrogen, $C_{1-6}$alkyl, aryl, heteroaryl$C_{1-6}$alkyl, heterocyclyl, heterocyclyl$C_{1-6}$alkyl, any of which except hydrogen can be optionally substituted or $R^2$ and $R^3$ together with the nitrogen atom to which they are attatched form an optionally substituted 5 or 6 membered monocyclic or bicyclic ring for example piperidine.

The compounds of formula (I) preferably have a molecular weight of less than 800.

Preferred substituents for the group Ar include halo, hydroxy, hydroxy $C_{1-6}$alkyl, hydroxyimino-$C_{1-6}$alkyl and $C_{1-6}$alkoxy.

It will be understood that the invention includes pharmaceutically acceptable derivatives of compounds of formula (I) and that these are included within the scope of the invention.

Particular compounds according to the invention include those mentioned in the examples and their pharmaceutically acceptable salts. As used herein "pharmaceutically acceptable derivatives" includes any pharmaceutically acceptable salt, ester or salt of such ester of a compound of formula (I) which, upon administration to the recipient, is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include those described in *J. Pharm. Sci.*, 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compounds of Formula (I) are imidazole derivatives which may be readily prepared using procedures well-known to those skilled in the art, and described in, for instance, Comprehensive Heterocyclic Chemistry, Editors Katritzky and Rees, Pergamon Press, 1984, 5, 457-497, from starting materials which are either commercially available or can be prepared from such by analogy with well-known processes. A key step in many such syntheses is the formation of the central imidazole nucleus.

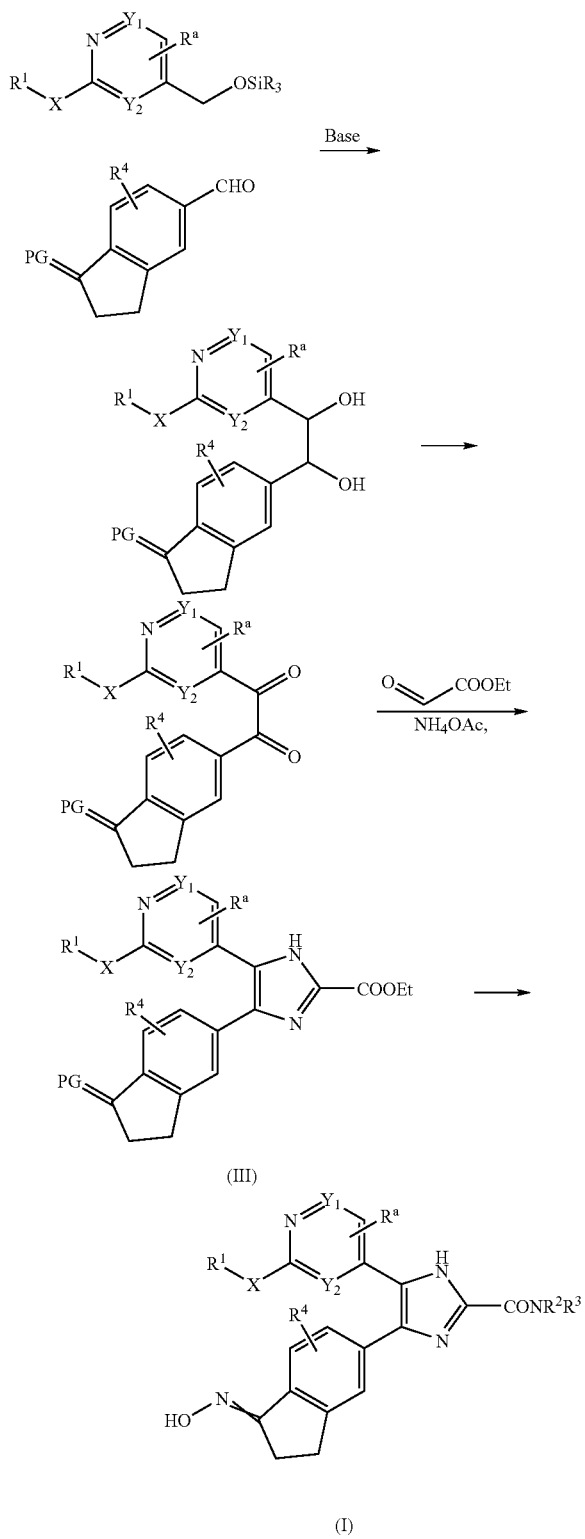

(III)

(I)

Preferred methods for preparing compounds of this invention are as outlined in the above scheme. α-Diketones are prepared by condensation of the anion of, for example, a 4-substituted pyridine derivative (Y$_1$=Y$_2$=CH, R$^1$—X=H and R$^4$=R$^a$=H) with a suitably protected fused bicyclic arylaldehyde (e.g. 1-methoxyimino-indan-5-carboxaldehyde) followed by oxidation of the intermediate product. Stirring the diketone with an aldehyde, such as glyoxylic acid ethyl ester, and ammonium acetate in a mixture of methanol and methyl-tert-butyl ether allows access to the imidazole nucleus, by analogy to the method described in patent WO 98/56788. Thereafter, the ethyl ester may be converted into an amide using conventional amide bond forming procedures (such procedures are well known in the art and are described in, for instance, P. D. Bailey, I. D. Collier and K. M. Morgan in *Comprehensive Organic Functional Group Transformation*, Vol. 5, ed. C. J. Moody, p.257, Elsevier Scientific, Oxford, 1995.) and the group PG converted into an hydroxyimono group (HO—N=).

Non-selective alkylation of the imidazole nitrogen (using one of the procedures outlined in N. J. Liverton et al; *J. Med. Chem.*, 1999, 42, 2180-2190) with a compound of formula L-R$^4$ wherein L is a leaving group, e.g. halo, sulfonate or triflate, will yield both isomers of the compounds where X$_1$ or X$_2$ is NR$^6$ in which R$^6$ is other than hydrogen, the isomers can be separated by chromatographic methods.

During the synthesis of the compounds of formula (I) labile functional groups in the intermediate compounds, e.g. hydroxy, carboxy and amino groups, may be protected. A comprehensive discussion of the ways in which various labile functional groups groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

The novel carboxylic esters and the corresponding acids of formula (II) and (III) which are used as intermediates in the synthesis of the compounds of formula (I) also form part of the present invention:

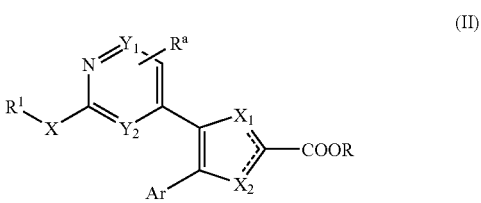

(II)

wherein X, Y$_1$, Y$_2$, R$^1$, R$^a$, Ar, X$_1$ and X$_2$ are as defined for formula (I) and R is hydrogen, C$_{1-6}$alkyl or arylC$_{1-6}$alkyl.

As indicated above the compounds of formula (I) and their pharmaceutically acceptable derivatives are useful for the treatment and/or prophylaxis of disorders in which Raf kinases, in particular B-Raf kinase, are implicated.

According to a further aspect of the invention there is provided the use of a compound of formula (I) or a pharmaceutically acceptable salt thereof as an inhibitor of B-Raf kinase.

As indicated above the compounds of formula (I) and their pharmaceutically acceptable derivatives are useful the treatment and/or prophylaxis of disorders associated with neuronal degeneration resulting from ischemic events.

According to a futher aspect of the invention there is provided a method of treatment or prophylaxis of a neurotraumatic disease, in a mammal in need thereof, which comprises administering to said mammal an effective amount of a compound of formula (I) or a pharmaceutically acceptable derivative thereof.

According to a futher aspect of the invention there is provided the use of a compound of formula (I) or a pharmaceutically acceptable derivative thereof in the manufacture of a medicament for the prophylactic or therapeutic treatment of any disease state in a human, or other mammal, which is exacerbated or caused by a neurotraumatic event.

Neurotraumatic diseases/events as defined herein include both open or penetrating head trauma, such as caused by surgery, or a closed head trauma injury, such as caused by an injury to the head region. Also included within this definition is ischemic stroke, particularly to the brain area, transient ischemic attacks following coronary by-pass and cognitive decline following other transient ischemic conditions.

Ischemic stroke may be defined as a focal neurologic disorder that results from insufficient blood supply to a particular brain area, usually as a consequence of an embolus, thrombi, or local atheromatous closure of the blood vessel. Roles for stress stimuli (such as anoxia), redox injury, excessive neuronal excitatory stimulation and inflammatory cytokines in this area has been emerging and the present invention provides a means for the potential treatment of these injuries. Relatively little treatment, for an acute injury such as these has been available.

The compounds of the invention may also be used in the treatment or prophylaxis of cancers.

In order to use the compounds of formula (I) in therapy, they will normally be formulated into a pharmaceutical composition in accordance with standard pharmaceutical practice.

According to a futher aspect of the invention there is provided a pharmaceutical composition comprising a compound of formula (I) or a pharmaceutically acceptable derivative thereof and a pharmaceutically acceptable carrier.

The compounds of formula (I) may conveniently be administered by any of the routes conventionally used for drug administration, for instance, parenterally, orally, topically or by inhalation. The compounds of formula (I) may be administered in conventional dosage forms prepared by combining it with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier is dictated by the amount of compound of formula (I) with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampoule or nonaqueous liquid suspension.

The compounds of formula (I) are preferably administered parenterally, that is by intravenous, intramuscular, subcutaneous intranasal, intrarectal, intravaginal or intraperitoneal administration. The intravenous form of parenteral administration is generally preferred. The compounds may be administered as a bolus or continuous infusion e.g. over 3 days. Appropriate dosage forms for such administration may be prepared by conventional techniques.

The compounds of formula (I) may also be administered orally. Appropriate dosage forms for such administration may be prepared by conventional techniques.

The compounds of formula (I) may also be administered by inhalation, that is by intranasal and oral inhalation administration. Appropriate dosage forms for such administration, such as aerosol formulations, may be prepared by conventional techniques.

The compounds of formula (I) may also be administered topically, that is by non-systemic administration. This includes the application of the inhibitors externally to the epidermis or the buccal cavity and the instillation of such a compound into the ear, eye and nose, such that the compound does not significantly enter the blood stream.

For all methods of use disclosed herein the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of the inhibitors will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the inhibitors given per day for a defined number of days, can be ascertained by those skilled in the art using conventional course of treatment determination tests. In the case of pharmaceutically acceptable salts the above figures are calculated as the parent compound of formula (I).

No toxicological effects are indicated/expected when a compound of formula (I) is administered in the above mentioned dosage range.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention and the following Descriptions illustrate the preparation of intermediates used in the preparation of these compounds.

Abbreviations uesd herein are as follows;
TBF means tetrahydrofuran.
DMF means N,N-Dimethylformamide.
LDA means lithium diisopropylamide.
TBAF means tetrabutylammonium fluoride.
DMSO means methyl sulfoxide.

DESCRIPTION

1: 4-(1-Oxo-indan-5-yl)-5-pyridin-4-yl-1H-imidazole-2-carboxylic Acid

Step 1. 5-Bromo-indan-1-one O-methyl-oxime

To a solution of 5-bromo-indanone (100 g, 0.474 mol) in ethanol (650 ml) under argon was added methoxylamine hydrochloride (198 g, 2.38 mol) and pyridine (125 ml). The mixture was refluxed for 2.5 hours, cooled to room temperature and poured into saturated aqueous sodium hydrogen carbonate solution. The mixture was then extracted with ethyl acetate and the organic phase dried ($Na_2SO_4$) and then concentrated in vacuo. The crude material was recrystallised from isopropanol to furnish the title compound, (110 g, 97%), as a brown solid; $^1$H NMR ($CDCl_3$) 7.52 (1H, d, J 8.3 Hz), 7.43 (1H, d, J 1 Hz), 7.35 (1H, dd, J 8.3, 1 Hz), 3.97 (3H, s), 2.99 (2H, m), 2.85 (2H, m).

Step 2. 1-Methoxyimino-indan-5-carbaldehyde

To a solution of the product of Step 1 (112 g, 0.46 mol) in THF (1500 ml) at −60° C. under argon, was added n-BuLi (325 ml, 0.52 mol) over 1 hour. After stirring at −60° C. for 1 hour a solution of DMF (39.7 ml) in THF (50 ml) was added dropwise over 1 hour. The reaction was stirred at −60° C. for 1 hour before being allowed to warm to room temperature. After 1 hour the reaction was quenched with saturated aqueous sodium hydrogen carbonate solution and extracted into ethyl acetate. The organic phase was then dried ($Na_2SO_4$), concentrated in vacuo and the residue purified by silica gel chromatography, to give the title compound (57 g, 65%) as a yellow solid; $^1$H NMR ($CDCl_3$) 10.0 (1H, s), 7.83-7.73 (3H, m), 4.02 (3H, s), 3.10 (2H, m), 2.92 (2H, m).

Step 3. 5-(1,2-Dihydroxy-2-pyridin-4-yl-ethyl)-indan-1-one-O-methyl-oxime

To a solution of 4-(tert-butyl-dimethyl-silyloxymethyl)-pyridine [T. F. Gallagher et al, *Bioorg. Med. Chem.*, 1997, 5, 49] (71.5 g, 0.32 mol) in THF (800 ml) at −50° C. under argon was added LDA (162 ml, 2M in heptane/THF/ethylbenzene, 0.324 mol) over 1 hour. The mixture was stirred at −40° C. for a further 1 hour before a solution of the product of Step 2 (55 g, 0.29 mol) in THF (600 ml) was added over 1 hour. The reaction was then allowed to warm to room temperature overnight before being quenched by the addition of saturated aqueous sodium hydrogen carbonate solution and then extracted into ethyl acetate. The organic phase was dried ($Na_2SO_4$) and concentrated in vacuo to give a brown oil (125 g).

The oil was then dissolved in THF (1500 ml), treated with TBAF (356 ml, 0.356 mol) and stirred for 1 hour. The reaction mixture was then evaporated and the residue partitioned between water and ethyl acetate. The organic phase was then dried ($Na_2SO_4$) and concentrated to give the title compound (57 g, 64%) as a pale yellow solid which was used without further purification. $^1$H NMR ($CDCl_3$) 8.38 (2H, m), 7.57 (1H, m), 7.12-6.99 (4H, m), 4.88 (1H, m), 4.66 (1H, m), 3.96 (3H, s), 2.93 (2H, m), 2.85 (2H, m).

Step 4. 1-(1-Methoxyimino-indan-5-yl)$_2$-pyridin-4-yl-ethane-1,2-dione

To a mixture of DMSO (43 ml, 0.56 mol) and dichloromethane (800 ml) at −70° C. under argon, was added oxalyl chloride (43.2 g) and then a solution of the product of Step 3 (55 g, 0.185 mol) in a mixture of dichloromethane/DMSO (1000 ml/60 ml) over 2 hours at −60° C. After stirring for 2 hours at −60° C., triethylamine (154 ml) was added dropwise and the mixture then allowed to warm to room temperature overnight. The reaction mixture was then quenched with water, the organic phase separated then washed with water, dried ($Na_2SO_4$) and concentrated to yield the title compound (51 g, 94%) as a yellow solid. $^1$H NMR ($CDCl_3$) 8.87 (2H, d), 7.89-7.77 (5H, m), 4.03 (3H, s), 3.09 (2H,m), 2.93 (2H, m).

Step 5. 4-(1-Methoxyimino-indan-5-yl)-5-pyridin-4yl-1H-imidazole-2-carboxylic Acid Ethyl Ester A mixture of the product of Step 4 (4.3 g, 15 mmol) and glyoxylic acid ethyl ester (50% solution in toluene, 6 ml, 30 mmol) in tert-butyl-methyl ether (150 ml) at 5° C. was treated with a solution of ammonium acetate (11.2 g, 145 mmol) in methanol (50 ml). After stirring at room temperature for 2 hours the solution was evaporated in vacuo and the residue was partitioned between chloroform and saturated sodium hydrogen carbonate solution. The organic layer was separated, washed with water and brine, dried $MgSO_4$), filtered and concentrated at reduced pressure. Purification of the residue by chromatography on silica gel eluting with 5% methanol in chloroform gave the title compound as a yellow solid (1.0 g, 18%); MS(AP+) m/e 377 [M+H]$^+$.

Step 6. 4-(1-Oxo-indan-5-yl)-5-pyridin-4-yl-1H-imidazole-2-carboxylic Acid Ethyl Ester Dihydrochloride Salt A mixture of the product of Step 5 (1.0 g, 2.7 mmol) and 5M HCl (15 ml) in dioxane (30 ml)/acetone (30 ml) was heated to 100° C. for 3 hour. The mixture was cooled to room temperature and the solvent evaporated in vacuo. The residue was co-evaporated with acetone (2×20 ml) and ethanol/acetone (1:1, 20 ml) to give the title compound (1.0 g, 88%); MS(ES$^-$) m/e 346 [M−H]$^-$.

Step 7. 4-(1-Oxo-indan-5-yl)-5-pyridin-4-yl-1H-imidazole-2-carboxylic Acid

A solution of the product of Step 6 (1.0 g, 2.4 mmol) in ethanol (10 ml) containing, 10% aqueous sodium hydroxide solution (10 ml) was heated at 50° C. overnight. On cooling, the solvent was removed in vacuo, the residue dissolved in water and the pH adjusted to 6 with glacial acetic acid and the solvent re-evaporated. The residue was suspended in water (50 ml) and the solid was collected, washed with water and dried over phosphorous pentoxide to give the crude title compound as an off-white solid (0.7 g); MS(AP$^-$) m/e 318 [M−H]$^-$.

EXAMPLE 1

4-(1-Hydroxyimino-indan-5-yl)-5-pyridin-4-yl-1H-imidazole-2-carboxylic Acid (2-morpholin-4-yl-ethyl)-amide

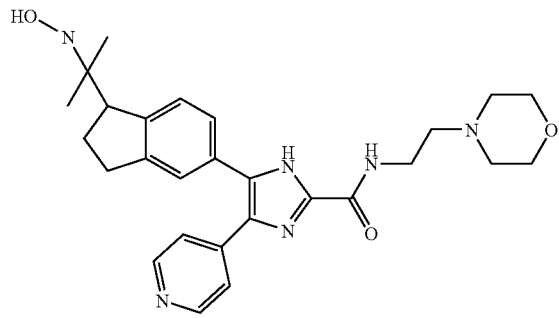

Step 1. 4-(1-Oxo-indan-5-yl)-5-pyridin-4-yl-1H-imidazole-2-carboxylic Acid (2-morpholin-4-yl-ethyl)-amide A mixture of the product of Description 1 (105 mg, 0.33 mmol), 1-hydroxybenzotriazole (68 mg, 0.5 mmol) and N-cyclohexylcarbodiimide-N'-methyl polystyrene (500 mg, 0.66 mmol, resin loading 1.32 mmol/g) in DMF (2 ml) was stirred at room temperature for 30 minutes. A solution of 2-morpholin-4-yl-ethylamine (43 mg, 0.33 mmol) in dichloromethane (0.5 ml) was added and the mixture stirred at room temperature for 24 hours. The mixture was filtered through an SCX cation exchange resin column eluting with methanol followed by 10% 0.880 ammonia solution in methanol to elute the product. Following concentration, the residue was purified by silica gel chromatography eluting with a 1:9:90 mixture of 0.880 ammonia solution: methanol: chloroform gave the title compound (65 mg, 46%) as a yellow solid; MS(AP+) m/e 432 [M+H]$^+$.

Step 2. 4-(1-Hydroxyimino-indan-5-yl)-5-pyridin-4-yl-1H-imidazole-2-carboxylic Acid (2-morpholinyl-ethyl)-amide A solution of the product of Step 1 (65 mg, 0.15 mmol) in ethanol (4 ml) and aqueous hydroxylamine (1 ml, 50% in water) was heated under reflux for 1 hour. After cooling to room temperature, the solution was concentrated in vacuo and the residue co-evaporated with ethanol (3×10 ml). Purification of the residue by silica gel chromatography eluting with a 1:9:90 mixture of 0.88 ammonia solution: methanol:chloroform gave the title compound (50 mg, 75%) as a yellow solid; MS(AP+) m/e 447 [M+H]$^+$.

The following examples were prepared from by the general two-step method described in Example 1.

| Example | | Amine | Characterisation |
|---|---|---|---|
| 2 | 5-(2-{1-[4-(2-Methoxy-ethyl)-piperazin-1-yl]-methanoyl}-5-pyridin-4-yl-1H-imidazol-4-yl)-indan-1-one oxime | 1-(2-Methoxy-ethyl)-piperazine | MS(AP+) m/e 461 [M + H]$^+$ |
| 3 | 4-(1-Hydroxyimino-indan-5-yl)-5-pyridin-4-yl-1H-imidazol-2-carboxylic acid methyl-(1-methyl-piperidin-4-yl)-amide | Methyl-(1-methyl-piperidin-4-yl)-amine | MS(AP+) m/e 445 [M + H]$^+$ |
| 4 | 5-{2-[1-(4-Cyclohexyl-piperazin-1-yl)-methanoyl]-5-pyridin-4-yl-1H-imidazol-4-yl}-indan-1-one oxime | 1-Cyclohexyl-piperazine | MS(AP+) m/e 485 [M + H]$^+$ |
| 5 | 5-[2-(1-[1,4']-Bipiperidinyl-1'-yl-methanoyl)-5-pyridin-4-yl-1H-imidazol-4-yl]-indan-1-one oxime | 4-Piperidino-piperidine | MS(AP+) m/e 485 [M + H]$^+$ |
| 6 | 5-(2-{1-[4-(4-Chloro-benzyl)-piperazin-1-yl]-methanoyl}-5-pyridin-4-yl-1H-imidazol-4-yl)-indan-1-one oxime | 1-(4-Chloro-benzyl)-piperazine | MS(AP+) m/e 453 [M + H]$^+$ |
| 7 | 4-(1-Hydroxyimino-indan-5-yl)-5-pyridin-4-yl-1H-imidazol-2-carboxylic acid (3-dimethylaminomethyl-phenyl)-amide | 3-Dimethylamino-methyl-phenylamine | MS(AP+) m/e 467 [M + H]$^+$ |
| 8 | 4-(1-Hydroxyimino-indan-5-yl)-5-pyridin-4-yl-1H-imidazol-2-carboxylic acid [4-(2-diisopropylamino-ethoxy)-3-methoxy-phenyl]-methyl-amide | [4-(2-Diisopropyl-amino-ethoxy)-3-methoxy-phenyl]-methyl-amine | MS(AP+) m/e 597 [M + H]$^+$ |

It is to be understood that the present invention covers all combinations of particular and preferred subgroups described hereinabove.

BIOLOGICAL EXAMPLES

The activity of compounds of formula (I) as B-Raf inhibitors may be determined by the following in vitro assay:

Fluorescence Anisoptrophy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×Ki) of a potent inhibitor the anisotropy of the unbound fluorescent ligand is measurably different from the bound value.

The concentration of kinase enzyme should preferably be $\geq 1 \times K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All compounds dissolved in Buffer of comparison 50 mM HEPES, pharmaceutical 7.5, 1 mM CHAPS, 10 mM MgCL$_2$.

B-Raf Enzyme concentration: 1 nM

Fluorescent ligand concentration: 0.5 nM

Test compound concentration: 0.5 nM-100 uM

Components incubated in 10 ul final volume in LJL HE 384 type B black microtitre plate until equilibrium reached (Over 3 h, up to 30 h)

Fluorescence anisotropy read LJL Acquest.

Definitions: Ki=dissociation constant for inhibitor binding
Kf=dissociation constant for fluorescent ligand binding
The fluorescent ligand is the following compound:

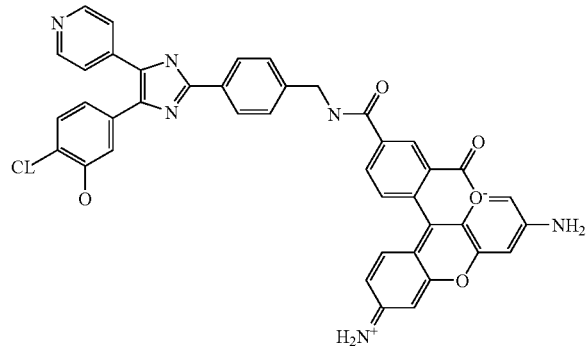

which is derived from 5-[2-(4-aminomethylphenyl)-5-pyridin-4-yl-1H-imidazol-4-yl]-2-chlorophenol and rhodamine green.

Compounds of the invention have a $K_d$ of less than 1 μM.

Raf Kinase Assay

Activity of human recombinant B-Raf protein was assessed in vitro by assay of the incorporation of radiolabelled phosphate to recombinant MAP kinase (MEK), a known physiologic substrate of B-Raf. Catalytically active human recombinant B-Raf protein was obtained by purification from sf9 insect cells infected with a human B-Raf recombinant baculovirus expression vector. To ensure that all substrate phosphorylation resulted from B-Raf activity, a catalytically inactive form of MEK was utilised. This protein was purified from bacterial cells expression mutant inactive MEK as a fusion protein with glutathione-S-transferase (GST-kdMEK).

Method: Standard assay conditions of B-Raf catalytic activity utilised 3 ug of GST-kdMEK, 10 uM ATP and 2 uCi $^{33}$P-ATP, 50 mM MOPS, 0.1 mM EDTA, 0.1M sucrose, 10 mM $MgCl_2$ plus 0.1% dimethylsulphoxide (containing compound where appropriate) in a total reaction volume of 30 ul. Reactions were incubated at 25° C. for 90 minutes and reactions terminated by addition of EDTA to a final concentration of 50 uM. 10 ul of reaction was spotted to P30 phosphocellulose paper and air dried. Following four washes in ice cold 10% trichloroacetic acid, 0.5% phosphoric acid, papers were air dried prior to addition of liquid scintillant and measurement of radioactvity in a scintillation counter.

Results: The compounds of the examples were found to be effective in inhibiting B-Raf mediated phosphorylation of GST-kdMEK substrate having $IC_{50}$'s of <3 μM.

The activity of compounds as Raf inhibitors may also be determined by the assays described in WO 99/10325; McDonald, O. B., Chen, W. J., Ellis, B., Hoffman, C., Overton, L., Rink, M., Smith, A., Marshall, C. J. and Wood, E. R. (1999) A scintillation proximity assay for the Raf/MEK/ERK kinase cascade: high throughput screening and identification of selective enzyme inhibitors, Anal. Biochem. 268: 318-329 and AACR meeting New Orleans 1998 Poster 3793.

The neuroprotective properties of B-Raf inhibitors may be determined by the following in vitro assay:

Neuroprotective Properties of B-Raf Inhibitors in Rat Hippocampal Slice Cultures Organotypic cultures provide an intermediate between dissociated neuronal cell cultures and in-vivo models of oxygen and glucose deprivation (OGD). The majority of glial-neuronal interactions and neuronal circuitry are maintained in cultured hippocampal slices, so facilitating investigation of the patterns of death among differing cell types in a model that resembles the in vivo situation. These cultures allow the study of delayed cellular damage and death 24 hours, or more, post-insult and permit assessment of the consequences of long-term alterations in culture conditions. A number of laboratories have reported delayed neuronal damage in response to OGD in organotypic cultures of the hippocampus (Vornov et al., Stroke, 1994, 25, 57465; Newell et al., Brain Res., 1995, 676, 38-44). Several classes of compounds have been shown to protect in this model, including EAA antagonists (Strasser et al., Brain Res., 1995, 687, 167-174), Na channel blockers (Tasker et al., J. Neurosci., 1992, 12, 98-4308) and Ca channel blockers (Pringle et al., Stroke, 1996, 7, 2124-2130). To date, relatively little is known of the roles of intracellular kinase mediated signalling pathways in neuronal cell death in this model.

Method: Organotypic hippocampal slice cultures were prepared using the method of Stoppini et al., J. Neurosci. Methods, 1995, 37, 173-182. Briefly, 400 micron sections prepared from hippocampi of 7-8 day postnatal Sprague Dawley rats are cultured on semiporous membranes for 9-12 days. OGD is then induced by incubation in serum and glucose-free medium in an anaerobic chamber for 45 minutes. Cultures are then returned to the air/$CO_2$ incubator for 23 hours before analysis. Propidium iodide (PI) is used as an indicator of cell death. PI is non toxic to neurones and has been used in many studies to ascertain cell viability. In damaged neurons PI enters and binds to nucleic acids. Bound PI shows increased emission at 635 nm when excited at 540 nm. One PI fluorescence image and one white light image are taken and the proportion of cell death analysed. The area of region CA1 is defined from the white light image and superimposed over the PI image. The PI signal is thresholded and area of PI damage expressed as a percentage of the CA1 area. Correlation between PI fluorescence and histologically confirmed cell death has been validated previously by Nissl-staining using cresyl fast violet (Newell et al., J. Neurosci., 1995, 15, 7702-7711).

It is to be understood that the present invention covers all combination of particular and preferred groups described herein above.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of composition, process, or use claims and may include by way of example and without limitation the following claims.

What is claimed is:

1. A compound of formula (I):

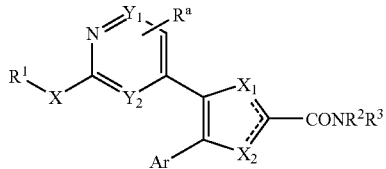

wherein:

X is O, CH$_2$, S or NH, or the moiety X-R$^1$ is hydrogen;

Y$_1$ and Y$_2$ independently represent CH;

R$^1$ is hydrogen, C$_{1-6}$alkyl, C$_{3-7}$cycloalkyl, aryl, arylC$_{1-6}$alkyl, any of which except hydrogen is unsubstituted or substituted with substituent or substituents as defined below;

R$^2$ and R$^3$ independently represent hydrogen, heterocyclyl, or heterocyclylC$_{1-6}$alkyl-, wherein the heterocycl or heterocyclylC$_{1-6}$alkyl is morpholine;

Ar is a group of the formula a) or b):

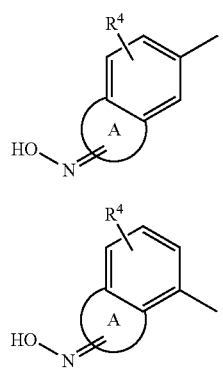

wherein A represents a fused 5 membered ring;

R$^a$ and R$^4$ are independently selected from hydrogen, halogen, C$_{1-6}$alkyl, aryl, arylC$_{1-6}$alkyl, C$_{1-6}$alkoxy, C$_{1-6}$alkoxyC$_{1-6}$alkyl, haloC$_{1-6}$alkyl, arylC$_{1-6}$alkoxy, hydroxy, nitro, cyano, azido, amino, mono- and di-N—C$_{1-6}$alkylamino, acylamino, arylcarbonylamino, acyloxy, carboxy, carbamoyl, mono- and di-N—C$_{1-6}$alkylcarbamoyl, C$_{1-6}$alkoxycarbonyl, aryloxycarbonyl, ureido, guanidino, C$_{1-6}$alkylguanidino, amidino, C$_{1-6}$alkylamidino, sulphonylamino, aminosulphonyl, C$_{1-6}$alkylthio, C$_{1-6}$alkyl sulphinyl or C$_{1-6}$alkylsulphonyl; and one of X$_1$ and X$_2$ is N and the other is NR$^6$, wherein R$^6$ is hydrogen, C$_{1-6}$alkyl, or arylC$_{1-6}$alkyl;

or a pharmaceutically acceptable salt thereof wherein the substituent or substituents for C$_{1-6}$alkyl or C$_{1-6}$cycloalkyl of R$^1$ as defined above is or are selected from:

aryl, C$_{1-6}$alkoxy, C$_{1-6}$alkylthio, arylC$_{1-6}$alkoxy, aryl C$_{1-6}$alkylthio, amino, mono- or di-C$_{1-6}$alkylamino, aminosulphonyl, cycloalkyl, cycloalkenyl, COOH, amide, ureido, guanidino, C$_{1-6}$alkylguanidino, amidino, C$_{1-6}$alkylamidino, hydroxy, and halogen or a combination thereof; and wherein the substituent or substituents for an aryl, arylC$_{1-6}$alkyl, of R$^1$ as defined above is or are selected from:

halogen, C$_{1-6}$alkyl, aryl, aryl C$_{1-6}$alkyl, C$_{1-6}$alkoxy, C$_{1-6}$alkoxy C$_{1-6}$alkyl, haloC$_{1-6}$alkyl, aryl C$_{1-6}$alkoxy, hydroxy, nitro, cyano, azido, amino, mono- and di-N—C$_{1-6}$alkylamino, acylamino, arylcarbonylamino, COOH, carbamoyl, mono- and di-N—C$_{1-6}$alkylcarbamoyl, C$_{1-6}$alkoxycarbonyl, aryloxycarbonyl, ureido, guanidino, C$_{1-6}$alkylguanidino, amidino, C$_{1-6}$alkyl amidino, sulphonylamino, aminosulphonyl, C$_{1-6}$alkylthio, C$_{1-6}$alkylsulphinyl, C$_{1-6}$alkylsulphonyl, or hydroxyimino-C$_{1-6}$alkyl or a combination thereof.

2. A compound according to claim 1 wherein X—R$^1$ is hydrogen or X is N—H, provided that when X is N—H, R$^1$ is hydrogen or C$_{1-6}$-alkyl.

3. A compound selected from:
4-(1-Hydroxyimino-indan-5-yl)-5-pyridin-4-yl-1H-imidazole-2-carboxylic acid (2-morpholin-4-yl-ethyl)-amide; or
a pharmaceutically acceptable salt thereof.

4. A pharmaceutical composition comprising a compound according to claim 1 or a pharmaceutically acceptable salt thereof and a pharmaceutically acceptable carrier.

5. A pharmaceutical composition comprising a compound according to claim 3 or a pharmaceutically acceptable salt thereof and a pharmaceutically acceptable carrier.

* * * * *